United States Patent
Freije et al.

(10) Patent No.: US 8,658,369 B2
(45) Date of Patent: *Feb. 25, 2014

(54) METHODS FOR EVALUATING THE METHYLATION STATUS OF A POLYNUCLEOTIDE

(71) Applicant: Euclid Diagnostics LLC, Crown Point, IN (US)

(72) Inventors: Wadiha Freije, Forest Park, IL (US); Igor Brikun, Forest Park, IL (US)

(73) Assignee: Euclid Diagnostics LLC, Crown Point, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/752,002

(22) Filed: Jan. 28, 2013

(65) Prior Publication Data

US 2013/0130259 A1   May 23, 2013

Related U.S. Application Data

(63) Continuation of application No. 12/649,169, filed on Dec. 29, 2009, now Pat. No. 8,361,724, which is a continuation of application No. PCT/US2008/069069, filed on Jul. 2, 2008.

(60) Provisional application No. 60/947,600, filed on Jul. 2, 2007.

(51) Int. Cl.
 *C12Q 1/68* (2006.01)
 *C12P 19/34* (2006.01)

(52) U.S. Cl.
 USPC ......... 435/6.12; 435/6.1; 435/6.11; 435/6.17; 435/6.18; 435/91.2

(58) Field of Classification Search
 None
 See application file for complete search history.

(56) References Cited

U.S. PATENT DOCUMENTS

| | | | |
|---|---|---|---|
| 6,287,825 B1 | 9/2001 | Weissman et al. | |
| 6,331,393 B1 | 12/2001 | Laird et al. | |
| 6,514,698 B1 | 2/2003 | Lopez et al. | |
| 6,911,306 B1 | 6/2005 | Vertino | |
| 7,112,404 B2 | 9/2006 | Laird et al. | |
| 8,361,724 B2* | 1/2013 | Freije et al. | 435/6.12 |
| 2002/0197639 A1 | 12/2002 | Shia et al. | |
| 2005/0153296 A1 | 7/2005 | Berlin | |
| 2006/0166206 A1 | 7/2006 | Urnov et al. | |
| 2006/0257905 A1 | 11/2006 | Freije et al. | |
| 2008/0213791 A1 | 9/2008 | Freije et al. | |

FOREIGN PATENT DOCUMENTS

| | | |
|---|---|---|
| EP | 1 568 786 A2 | 8/2005 |
| WO | WO 03/080862 A1 | 10/2003 |
| WO | WO 03/080863 A1 | 10/2003 |
| WO | WO 2005/033332 A2 | 4/2005 |
| WO | WO 2007/033834 A2 | 3/2007 |
| WO | WO 2007/102891 A2 | 9/2007 |
| WO | WO 2009/006543 A1 | 1/2009 |

OTHER PUBLICATIONS

Cairns et al., *Clinical Cancer Research*, 7: 2727-2730 (2001).
Eads et al., *Nucleic Acids Research*, 28(8): i-vii (2000).
Frommer et al., *Proc. Natl. Acad. Sci. U.S.A.*, 89: 1827-1831 (1992).
Galm et al., *Genome Research*, 12(1): 153-157 (2002).
Goessl et al., *Cancer Research*, 60: 5941-5945 (2000).
Gonzalgo et al., *Clin. Cancer Res.*, 9: 2673-2677 (2003).
Goyal et al., *Nucleic Acids Research*, 34(4): 1182-1188 (2006).
Matin et al., *Human Mutation*, 20: 305-311 (2002).
Smith et al., *Nucleic Acids Research*, 35(3): 740-754 (2007).
Xiong et al., *Nucleic Acids Research*, 25: 2532-2534 (1997).
European Patent Office, International Search Report in International Patent Application No. PCT/US2008/069069 (Nov. 7, 2008).
European Patent Office, Written Opinion in International Patent Application No. PCT/US2008/069069 (Nov. 7, 2008).

* cited by examiner

*Primary Examiner* — Angela M Bertagna
(74) *Attorney, Agent, or Firm* — Leydig, Voit & Mayer, Ltd.

(57) ABSTRACT

The invention provides methods related to evaluating the methylation status of a polynucleotide that includes an internal control.

17 Claims, No Drawings

METHODS FOR EVALUATING THE METHYLATION STATUS OF A POLYNUCLEOTIDE

CROSS-REFERENCE TO RELATED APPLICATIONS

This patent application is a continuation of copending U.S. patent application Ser. No. 12/649,169, scheduled to issue on Jan. 29, 2013 as U.S. Pat. No. 8,361,724, which is continuation of U.S. International Patent Application No. PCT/US2008/069069, filed Jul. 2, 2008, which claims the benefit of U.S. Provisional Patent Application No. 60/947,600, filed Jul. 2, 2007, which are hereby incorporated by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 4,751 Byte ASCII (Text) file named "712183SequenceListing.TXT," created on Jan. 25, 2013.

BACKGROUND OF THE INVENTION

Phosphate linked cytosine-guanine (CpG) dinucleotides are statistically underrepresented in the human genome. When they are present, CpG dinucleotides tend to be located within repetitive sequences characterized by low levels of gene expression. Such CpG dinucleotides also tend to feature a methylated cytosine residue.

CpG islands, on the other hand, are genomic sequences with a high density of CpG dinucleotides relative to the rest of the genome. CpG islands include statistical clusters of CpG dinucleotides. While some CpG islands are associated with the promoter region or 5' end of coding sequences, others are located in introns or genomic regions not known to be associated with coding sequences. CpG islands may be methylated or unmethylated in normal tissues. The methylation pattern of CpG islands may control the expression of tissue specific genes and imprinted genes. Methylation of CpG islands within a gene's promoter regions has been associated with downregulation or silencing of the associated gene. CpG islands may be methylated to varying densities within the same tissue. An increase in methylation of normally unmethylated CpG islands is observed in aging tissues, even as the overall methylcytosine content of the DNA is reduced.

Aberrant methylation patterns are especially notable in cancer cells. For example, hypermethylation has been detected in a number of cancer tissues. Aberrant methylation of cytosines within CpG islands may be a primary epigenetic event that acts to suppress the expression of genes involved in critical cellular processes, such as DNA damage repair, hormone response, cell-cycle control, and tumor-cell adhesion/metastasis, leading to tumor initiation, progression, and metastasis (Li et al., *Biochim. Biophys. Acta*, 1704: 87-102 (2004)). Aberrant methylation of CpG islands may also be a secondary epigenetic event or a symptom of an upstream abnormality that is the primary event leading to cancer.

It has been proposed that a unique profile of promoter methylation exists for each human cancer, wherein some methylation characteristics are shared and others are cancer-type specific (Esteller et al., *Cancer Res.*, 61: 3225-3229 (2001), U.S. Pat. No. 7,112,404, and U.S. Patent Application Publication Nos. 2005/0153296 and 2005/0164193). Given that aberrant methylation represents new information not normally present in genomic DNA and that aberrant methylation is a common DNA modification and affects a large number of genomic targets, a number of diagnostic and prognostic tests may be developed that assay for the methylation status of one or more target CpGs. Such tests may be based on CpGs that are aberrantly hypermethylated or hypomethylated in diseased tissues. They may also be based on changes in methylation density in CpG islands. Target CpGs can correlate with a risk for cancer, the presence of cancer, or a particular cancer phenotype, such as prognosis or response profile to treatment regimen.

In addition to selecting appropriate target CpGs, the reliability and cost-effectiveness of CpG methylation diagnostic and prognostic tests may also be improved through the use of appropriate controls that provide information about the integrity of the reagents, equipment, and underlying reactions on which the methylation test depends.

Methods for analyzing nucleic acid methylation that include separate, external controls have been described. For example, WO 2007/033834 describes using a parallel, in vitro methylated nucleic acid as a positive control. The positive control is generated by separating an aliquot of genomic DNA and methylating the separated DNA with a methyl transferase, i.e., a methylase, which preferably methylates sequences within specific sequence recognition sites. In this regard, the disclosed method preferably includes using M.SssI methylase, which preferentially methylates cytosines in CpG dinucleotides, to generate positive controls for analyzing CpG methylation in genomic DNA.

Improved controls for use in methylation analysis are highly desirable, for example, in high throughput diagnostic and prognostic tests, where efficiencies related to the smaller reaction numbers, reduced reagent consumption, and increased confidence in test results may be especially valuable. Improved test controls are also highly desirable in diagnostic and prognostic tests for methylation of samples that include small amounts of DNA such as, for example, circulating DNA in bodily fluid samples.

BRIEF SUMMARY OF THE INVENTION

The invention relates to methods for assaying the methylation status of a polynucleotide that include an internal control. Generally, the methods of the invention are directed to analyzing the methylation status of one or more target nucleotides in one or more target sequences in a sample. Optionally, the one or more polynucleotides are purified from the sample, thereby generating a purified polynucleotide. Optionally, the one or more polynucleotide target sequences are amplified, and the methylation status of the target sequence is copied in the amplified target sequences, thereby generating amplified polynucleotides with target sequences. The sample, the purified polynucleotide, or the amplified polynucleotide is treated with a methylase that preferentially methylates one or more control sequence nucleotides in the target sequence. Subsequently, the method includes assaying for the methylation status of the one or more target nucleotides and the one or more control sequence nucleotides in the target sequence. Methylation at the one or more control sequence nucleotides indicates the presence of the target sequence and successful sample preparation (e.g., purification and/or amplification) and successful assaying for methylation. The absence of methylation at the one or more control sequence nucleotides indicates a technical failure in the assaying for methylation. Technical failures can be due, for example, to an insufficient amount of polynucleotide comprising the target sequence in the original sample, failure to purify or amplify the target sequence, and/or failure of a reagent.

Thus, the invention includes a method for analyzing the methylation status of a target sequence in a sample with an internal control for detecting the presence of the target sequence. The method includes providing a sample that includes DNA, optionally purifying the DNA, and optionally amplifying the DNA and simultaneously copying the methylation pattern of the DNA to produce amplified DNA. The sample, purified DNA, or amplified DNA is treated with a methylase that preferentially methylates at one or more control sequence nucleotides in the target sequence. The method subsequently includes assaying for the methylation status of (i) the one or more control nucleotide and (ii) one or more CpG dinucleotides in the target sequence in the sample, purified DNA, or amplified DNA. Methylation at the one or more control sequence nucleotides indicates the presence of the target sequence in the sample, and the presence or absence of methylation at the one or more CpG dinucleotides indicates the presence or absence, respectively, of methylation at the corresponding dinucleotides in the sample. Alternatively, the absence of methylation at the one or more control sequence nucleotides indicates the absence of the target sequence in the sample, purified DNA, or amplified DNA and/or a technical failure.

The invention also includes a method for analyzing the methylation status of a target sequence in a sample with an internal control for detecting the presence of the target sequence. The method includes providing a sample that includes DNA, optionally purifying the DNA, and optionally amplifying the DNA and simultaneously copying the methylation pattern of the DNA to produce amplified DNA. The sample, purified DNA, or amplified DNA is treated with a methylase that preferentially methylates at one or more control sequence nucleotides in the target sequence. The method subsequently includes using terminator-coupled linear amplification suitable for generating extension products that indicate (i) the methylation status of one or more CpG dinucleotides in the target sequence and (ii) the methylation status of the one or more control sequence nucleotides in the treated sample, purified DNA, or amplified DNA. Methylation at the one or more control sequence nucleotides indicates the presence of the target sequence in the sample; and the presence or absence of methylation at the one or more CpG dinucleotides indicates the presence or absence, respectively, of methylation at the corresponding dinucleotides in the sample. Alternatively, the absence of methylation at the one or more control sequence nucleotides indicates the absence of the target sequence in the sample, purified DNA, or amplified DNA and/or another technical failure.

Furthermore, the invention includes a method for evaluating the density of DNA methylation in a target sequence with an internal control for detecting the presence or absence of the target sequence. The method includes providing a sample that includes DNA, optionally purifying the DNA, and optionally amplifying the DNA and simultaneously copying the methylation pattern of the DNA to produce amplified DNA. The sample, purified DNA, or amplified DNA is treated with a methylase that preferentially methylates at one or more control sequence nucleotides in the target sequence. The method subsequently includes using terminator-coupled linear amplification to generate extension products from the treated sample, purified DNA, or amplified DNA and assaying for the lengths of the extension products that indicate the methylation status of (i) more than one CpG dinucleotide and (ii) one or more control sequence nucleotides in the target sequence. The presence of methylation at the one or more control sequence nucleotides indicates the presence of the target sequence in the original sample and the number of methylated CpG dinucleotides indicates the density of DNA methylation in the target sequence. Alternatively, the absence of methylation at the one or more control sequence nucleotides indicates the absence of the target sequence in the sample, purified DNA, or amplified DNA and/or failure of the terminator-coupled linear amplification reaction.

Additionally, the invention includes a method of evaluating the fraction of polynucleotides comprising a methylated target sequence with an internal control for detecting the presence of the target sequence. The method includes providing a sample that includes DNA, optionally purifying the DNA, and optionally amplifying the DNA and simultaneously copying the methylation pattern of the DNA to produce amplified DNA. The sample, purified DNA, or amplified DNA is treated with a methylase that preferentially methylates at one or more control sequence nucleotides in the target sequence. The method subsequently includes using terminator-coupled linear amplification suitable for generating extension products that indicate (i) the methylation status of one or more CpG dinucleotides in the target sequence and (ii) the methylation status of the one or more control sequence nucleotides in the treated sample, purified DNA, or amplified DNA. The method further includes assaying for the length and amount of one or more extension products indicating the methylation status of one or more CpG dinucleotides in the target sequence. The amount of each such assayed extension product is compared to a corresponding amount in a standard generated from known amounts of methylated and unmethylated template. According to the method, the presence of methylation at the one or more control sequence nucleotides indicates the presence of the target sequence in the original sample; and each corresponding amount in the standard indicates the fraction of polynucleotides in the sample, purified DNA, or amplified DNA that comprise the corresponding methylated CpG dinucleotide in the target sequence. Alternatively, the absence of methylation at the one or more control sequence nucleotides indicates the absence of the target sequence in the sample, purified DNA, or amplified DNA and/or failure of the terminator-coupled linear amplification reaction.

The invention described herein further provides a method of preparing a sample for methylation analysis. Generally the method includes providing a sample with DNA, optionally, purifying the DNA and, optionally, amplifying the DNA. The sample, purified DNA, or amplified DNA is subsequently treated with a methylase that preferentially methylates cytosine residues within a recognition sequence larger than 2 nucleotides. According to the method the sample includes one or more of the following mammalian bodily fluids: blood, blood plasma, blood serum, urine, sputum, ejaculate, semen, tears, sweat, saliva, lymph fluid, bronchial lavage, pleural effusion, peritoneal fluid, meningal fluid, amniotic fluid, glandular fluid, fine needle aspirates, nipple aspirate fluid, spinal fluid, conjunctival fluid, vaginal fluid, duodenal juice, pancreatic juice, pancreatic ductal epithelium, pancreatic tissue bile, and cerebrospinal fluid.

DETAILED DESCRIPTION OF THE INVENTION

The invention provides methods for analyzing the methylation status of one or more target sequences in samples that include polynucleotides. As used herein, "target sequence" refers to a nucleotide sequence that includes one or more target nucleotides with a methylation status of interest. For example, target sequences include genomic CpG islands, or portions thereof, with one or more target cytosines whose methylation status is associated with a disease state. The methylation status of a target sequence refers to whether at least one target nucleotide (e.g., a target cytosine in a CpG dinucleotide) or at least one control nucleotide in the target sequence is methylated or unmethylated. Alternatively, methylation status of target sequence can refer to whether a multiple (i.e., a plurality of) target nucleotides or control sequence nucleotides in a target sequence are each methylated or unmethylated. When referring to multiple or a plurality of target nucleotides, methylation status can refer to the methylation pattern or methylation density of a target sequence.

The methods of the invention include an internal control, i.e., the one or more internal control sequence nucleotides described herein. As such, the methods are particularly useful in the methylation analysis of samples having relatively small amounts of genomic DNA, since none of the genomic DNA needs to be partitioned off for use in a separate, external control reaction. Accordingly, the methods are useful to avoid depleting the scarce genomic DNA in such samples.

The methods of the invention also reduce the total number of reactions that need to be processed and analyzed in a methylation assay. Since each analyzed sample provides its own internal control, there is also no need for a second external control reaction. Therefore, the methods of the invention allow more samples to be analyzed at the same time. Additionally, by avoiding the need for additional external control reactions, the methods of the invention also provide a way to reduce the amounts of reagents and other consumables (e.g., parts, sample containers, well plates, and such) needed to analyze a number of samples. In this regard, the methods of the invention can be advantageously used in conjunction with methods for high throughput methylation analysis.

The samples referenced herein can include DNA and, more particularly, genomic DNA. Samples can include tissue samples and cells, e.g., those acquired by biopsy or other techniques from an organism. Samples can also include tissues and cells cultured in vitro.

Samples can also include bodily fluids, which, generally, refer to mixtures of macromolecules obtained from an organism. Thus, samples can include blood, blood plasma, blood serum, urine, sputum, ejaculate, semen, tears, sweat, saliva, lymph fluid, bronchial lavage, pleural effusion, peritoneal fluid, meningal fluid, amniotic fluid, glandular fluid, fine needle aspirates, nipple aspirate fluid, spinal fluid, conjunctival fluid, vaginal fluid, duodenal juice, pancreatic juice, pancreatic ductal epithelium, pancreatic tissue bile, and cerebrospinal fluid. Samples can include solutions or mixtures made from homogenized solid material such as feces. Samples can include experimentally/clinically separated fractions from bodily fluids, tissues, and/or cells.

The methods of the invention are particularly useful for the methylation analysis of samples with relatively small amounts of genomic DNA, since the methods avoid the need to deplete sample DNA. For example, some samples can include 10, 9, 8, 7, 6, 5, 4, 3, 2, or 1 nanograms of DNA. Other samples can include as little as 500, 400, 300, 200, or 100 picograms of DNA. Such samples are exemplified by urine and plasma, which include relatively small amounts of circulating DNA. In this regard, the amount of circulating DNA recovered from different individuals can vary as much as 10-fold or more. Additionally, the methods of the invention are useful for the analysis of samples that include otherwise depleted or scarce genomic DNA.

Optionally, the sample polynucleotide, e.g. genomic DNA, can be purified. As used herein, "purified" refers to the separation of polynucleotide material from some or most of the tissue, cellular, macromolecular, or other non-polynucleotide material previously associated with the polynucleotide. Genomic DNA can include fragments of differing lengths, including fragments as short as 100 to 200 base pairs (bp) in length (as used herein, "bp" can also refer to the length, in nucleotides, of single stranded polynucleotides). In such cases, DNA can be ligated to generate larger non-contiguous fragments following enzymatic treatment to generate suitable ends. Also, optionally, the target sequence in a sample polynucleotide can be amplified in a way that copies or indicates the methylation status of the target sequence during amplification.

Amplification methods that have been used in connection with methylation analyses include polymerase chain reaction (PCR), real-time PCR, and isothermal amplification. PCR amplification or isothermal amplification methods include, for example, those described in U.S. Pat. Nos. 5,854,033; 6,124,120; 6,143,495; 6,210,884; 6,642,034; 6,280,949; 6,632,609; and 6,642,034; and U.S. Patent Application Publication Nos. 2003/0032024; 2003/0143536; 2003/0235849; 2004/0063144; and 2004/0265897, each of which is incorporated herein by reference in their entirety. Isothermal amplification can include rolling circle or strand displacement amplification. Methods that combine PCR and isothermal amplification have also been described in U.S. Pat. Nos. 6,777,187; and 6,828,098; and U.S. Patent Application Publication Nos. 2004/0209298; 2005/0032104; and 2006/0068394, each of which is incorporated herein by reference in its entirety. In each of the foregoing amplification methods, however, care should be taken to ensure that methylation status or information about the methylation status of the original polynucleotide is preserved during amplification.

Freije et al. (in U.S. Patent Application Publication No. 2006/0257905 A1, which is specifically incorporated by reference herein in its entirety) describes methylation-coupled isothermal amplification of genomic DNA molecules. Generally, Freije et al. discloses amplifying DNA using a polymerase with strand displacement activity and simultaneously copying the methylation status of the DNA using a methylation maintenance enzyme under conditions that promote both polymerase and methylation maintenance enzyme activity.

Additional considerations may be applicable to the simultaneous amplification and methylation of samples wherein (a) genomic DNA is present in a relatively small amount and/or (b) genomic DNA from the tissue source of interest (e.g., from a tumor) represents only a small fraction of the sample's genomic DNA. For example, the amount of DNA recovered from bodily fluids, such as plasma or urine, is usually only a few nanograms per milliliter (Jahr et al., *Cancer Res.*, 61(4): 1659-1665 (2001); and Anker et al., *Cancer Metastasis Rev.*, 18(1): 65-73 (1999)). The inventors have routinely recovered fewer than a few nanograms of circulating DNA per milliliter of urine and plasma. Moreover, while some cancer patients can exhibit higher levels of DNA in their bodily fluids, others have amounts comparable to those isolated from normal individuals. Although extracting a larger sample can increase the amount of DNA, there is usually a limited volume that can be reasonably obtained and analyzed in a clinical setting. In this regard, for example, consideration should be taken to reduce the de novo methylation activity towards CpG of methylase in vitro (see e.g., in Fatemi et al., *J. Mol. Biol.*, 309: 1189-1199 (2001); Pradham et al., *J. Biol. Chem.*, 274: 33002-33010 (1999); and Tollefsboll et al., *J. Mol. Biol.*, 269: 494-504 (1997)). This de novo activity can result in false positives by introducing methylated residues to target sequence nucleotides that were not methylated in the original sample DNA. Thus, the methods described herein preferably use a DNMT-1 methylase enzyme that lacks or has minimal activity towards unmethylated substrates to copy the methylation pattern of genomic DNA, especially when the genomic DNA is from a sample that includes a relatively small amount of genomic DNA, a small percentage of methylated residues in a particular target sequence, or both.

Furthermore, cancer detection and prognosis can require evaluating multiple markers (Yegnasubramanian et al., *Cancer Res.*, 64(6): 1975-86 (2004)) and multiple assays of the same marker(s). Even more markers are likely to be needed in cancer diagnostic assays from circulating DNA to achieve the sensitivity and specificity needed for clinical applications. Methylation analysis is further complicated by the heterogeneity of DNA methylation patterns in cancers which may differ between tumors derived from different tissues (Esteller, *Cancer Res.*, 61(8): 3225-9 (2001)) and between tumor cells derived from the same tissue (Zhao, *Cancer*, 104(1): 44-52 (2005)). Therefore, methylation-based cancer diagnosis may require the analysis of multiple CpG islands and multiple CpG dinucleotides across the length of an island. Such analyses are likely to require or benefit from the use of an internal control when there is a limited quantity of genomic DNA for analysis. Such analyses can also require or benefit from the amplification and simultaneous copying of the methylation pattern of DNA, for example, in bodily fluid samples.

The methods of the invention include treating a sample to be analyzed (e.g, a tissue sample, a bodily fluid sample, purified DNA, and/or amplified DNA) with a methylase that preferentially methylates one or more control sequence nucleotides in the target sequence of interest. A "control sequence nucleotide," as used herein, is a nucleotide within the target sequence that differs from the one or more target nucleotides with a methylation status of interest. A methylase that methylates the C5 position of cytosine residues within a relatively larger recognition sequence, such as HhaI and HpaII methylases (New England Biolabs ("NEB", Ipswhich, Mass.)), can be used to methylate control sequence nucleotides when, for example, (a) recognition sites for more convenient methylases are not available in the target sequence and (b) the target CpG dinucleotide of interest is not located within the relatively larger recognition sequence of such a methylase. Commercially available methylases listed in the REBASE database (see, e.g., Roberts et al., *Nucl. Acids Res.*, 35(Database issue): D269-D270 (2007) are set forth in Table 1.

TABLE 1

| Methylases | Recognition Sequence |
|---|---|
| M. AluI | AGCT |
| M. HaeIII | GGCC |
| M. Fsp4HI | GCNGC |
| M. HspAI | GCGC |
| M. HapII | CCGG |
| M. HhaI | GCGC |
| M. HpaII | CCGG |
| M. MspI | CCGG |

Convenient methylases for use in conjunction with certain methods described herein include Alu I, Hae III, and Msp I methylases (NEB), insofar as they preferentially methylate cytosines other than cytosines in CpG dinucleotides. Thus, these methylases can advantageously preserve CpG methylation information present in a target sequence, while preferentially methylating one or more control sequence nucleotides.

Subsequent to methylating control sequence nucleotides, the methods of the invention include assaying for the methylation status of (i) one or more target nucleotides in a target sequence and (ii) one or more control sequence nucleotides in the target sequence. Methods for assaying methylation status are known in the art.

One method according to the invention for assaying for the methylation status of a target or control cytosine nucleotide involves converting unmethylated cytosines to uracils in a DNA target sequence. Preferably the conversion includes treating the DNA with bisulfite under deaminating conditions. The resulting sequence differences following bisulfite treatment, which indicate the methylation status of target and/or control cytidines, can be detected, for example, by any suitable method. Such methods include one or more of the following methods: digestion with sequence specific restriction endonucleases followed by Southern blot analysis, digestion of the amplification product of bisulfite-treated sample DNA with sequence specific restriction endonucleases (combined bisulfite restriction analysis or "COBRA," Xiong et al., *Nucl. Acids Res.*, 25: 2532-2534 (1997), which is specifically incorporated herein by reference in its entirety), direct nucleotide sequencing (Frommer et al., *Proc. Nat'l Acad. Sci. USA*, 89: 1827-1831 (1992), which is specifically incorporated herein by reference in its entirety), methylation-specific PCR amplification (Herman et al., *Proc. Nat'l Acad. Sci. USA*, 93: 9821-9826 (1996), and U.S. Pat. Nos. 5,786,146 and 6,265,171, all of which are specifically incorporated herein by reference in their entireties), methylation-sensitive single nucleotide primer extension ("Ms-SNuPE") of oligonucleotides complementary to target DNA (Gonzalgo et al., *Nucl. Acids Res.*, 25: 2529-2531 (1997), and U.S. Pat. No. 6,251,594, which are specifically incorporated herein by reference in their entireties), semi-quantitative fluorescent-based real time PCR (Eads et al., *Nucl. Acids Res.*, 28: e32, i-viii (2000), which is specifically incorporated herein by reference in its entirety), quantitative real-time PCR (Rand et al., *Methods*, 27: 114-120 (2002), and U.S. Pat. Nos. 6,331,393; 5,494,810; and 6,268,148, which are specifically incorporated herein by reference in their entireties), headloop suppression PCR (Rand et al., *Nucl. Acids Res.*, 33: e127, 1-11 (2005), which is specifically incorporated herein by reference in its entirety), ligation-mediated amplification (Barany et al., *Proc. Nat'l Acad. Sci. USA*, 88(1): 189-193 (1991), and U.S. Pat. Nos. 5,494,810 and 6,268,148, all of which are specifically incorporated herein in their entireties), microarray analysis (Gitan, *Methods*, 12: 158-164 (2001); Schumacher, *Nucl. Acids Res.*, 34: 528-542 (2006); and U.S. Patent Application Publication Nos. 2003/0148326, 2003/0148327, and 2006/0068402, all of which are specifically incorporated herein by reference in their entireties), and mass spectrometry (Tost et al., *Clin. Biochem.*, 38(4): 355-50 (2005); and U.S. Patent Application Publication No. 2005/0089904, which are specifically incorporated herein by reference in their entireties).

Another method in accordance with the invention for assaying the methylation status of target and/or control sequence nucleotides includes the use of terminator-coupled linear amplification (Patent Cooperation Treaty Application No. PCT/US2006/060685 filed Nov. 8, 2006, and published as WO 2007/102891, which is specifically incorporated herein by reference in its entirety). Sample DNA is linearly amplified using a forward or a reverse primer in the presence of dNTPs, a polymerase, and one or two terminator dideoxynucleotides, (e.g., dideoxycytidine dideoxthymidine, dideoxyadenine, or dideoxyguanine). The linear amplification can, optionally, use only cytosine terminators when assaying for a methylated target CpG dinucleotide and/or a methylated control cytosine (or guanine terminators when analyzing the amplified strand opposite to the target or control nucleotide) to generate extension products that terminate at cytosine nucleotides (or at guanine nucleotides when assaying the opposite strand). Alternatively, linear amplification can use thymine (or adenine when analyzing the opposite strand) to generate extension products and assay for the absence or reduction in the signal at a specific target or control cytosine. However, a direct assay for the presence of cytosine (or guanine when analyzing the opposite strand) is preferred when the target sequence is heterogeneous. The generated extension products have various lengths, and each length corresponds to the distance in bases between the primer used for amplification and the position within the target sequence of a nucleotide that is complementary to the terminator dideoxynucleotide added to the amplification reaction. Such amplification can generate 10 to 20 extension products from an average CpG island-containing amplicon of 100 to 150 bp. Extension products can be separated by size (e.g., on an acrylamide gel or in a polymer filled capillary) and compared to (a) a size standard and/or (b) the size of fragments generated with from fully unmethylated (PCR generated template or clones in E. coli) or fully methylated (enzymatically methylated in vitro) control templates to thereby determine the presence of cytosine (or guanine on the opposite strand) residues or the presence of thymine (or adenine on the opposite strand) residues in the amplified target sequence.

When bisulfite is used as the deaminating agent, the amplified sequence may contain large stretches of thymine or adenine which produce artifactual amplification or extension products due to DNA polymerase slippage. During slippage, the polymerase repeatedly amplifies (i.e., inserts complementary nucleotides) the same nucleotide or block of nucleotides in a template strand. Therefore, slippage during PCR amplification, isothermal amplification, or linear amplification (such as in nucleotide sequencing or linear terminator-coupled amplification) can result in the production of amplified or extension products that are longer than they should be. Slippage is associated with "stutter" sequencing patterns. DNA polymerase slippage can be minimized by selectively analyzing segments of the CpG islands that have shorter homopolymeric sequences. Stutter amplification products can also be identified by analyzing methylated and unmethylated control templates.

When a fluoresent label is used to tag the primers or the dideoxynucleotides used in the terminator-coupled linear amplification, the resulting fragments may be analyzed using automated sequencing machines and software designed for determining the size of DNA fragments. In this regard, commercially available software, such as GENESCAN (Applied Biosystems, Foster City, Calif.) and GENEMAPPER (Applied Biosystems), can recognize and account for stutter patterns due to DNA polymerase slippage during the amplification of microsatellite repeats. Such software also can be used to account for the stutter pattern that is observed when amplifying homopolymeric stretches of DNA, as may occur after bisulfite conversion of CpG islands. There are a number of fluorescent dyes available for the automated analysis of DNA such as but not limited to 6-carboxyfluorescein (6-FAM), hexachlorofluorescein (HEX), VIC™ dye (Applied Biosystems), 5-carboxytetramethylrhodamine (TAMRA), 5-carboxy-X-rhodamine, succinimidyl ester (5-ROX), and 6-carboxy-2',4,7,7'-tetrachlorofluorescein (TET). The methods and equipment to determine amplicon size have been available for over a decade and have been used for genetic linkage mapping, DNA identity, and forensic. For example, Applied Biosystems has a set of 5 dyes that can be used to multiplex fragments from 4 separate amplification reactions and one standard for use in linkage mapping on the ABI sequencers. Four different CpG islands from a single individual can be linearly amplified using fluorescently tagged primers, and the products can be pooled before analysis. Alternatively, different CpG islands from different individuals can be linearly amplified using fluorescently tagged primers, and the products pooled before analysis.

The methods for introducing an internal control described herein also can be used to reduce DNA polymerase slippage and, thereby, prevent or reduce the production of stutter amplification products. In some embodiments, the methods of the invention include introducing a methylated cytosine at one or more control sequence nucleotides in the target sequence, wherein the control sequence nucleotide otherwise would correspond to an unmethylated cytosine, which following deamination and subsequent amplification otherwise would correspond to one or more thymines (or adenines in the opposite strand) in a large stretch of thymines (or adenines in the opposite strand). The introduction of methylated cytosine control sequence nucleotides to prevent their conversion to thymines can be used to interrupt what otherwise would be large stretches of thymines (or adenines) in deaminated and amplified target sequences. By reducing the length of such stretches, the methods of the invention can reduce the incidence of DNA slippage during amplification of a target sequence, e.g. during PCR, isothermal amplification, sequencing, or terminator-coupled linear amplification.

The methods of the invention can be used to analyze the percent or extent of methylation of a particular target or control nucleotide in a target sequence (with a methylated control sequence nucleotide) in a sample. These methods are useful in the analysis of samples that include non-uniformly or heterogeneously methylated polynucleotides comprising the target sequence.

The following describes one method for analyzing the percent or extent of methylation of a particular target nucleotide (e.g., a target cytosine in a genomic CpG dinucleotide) in a sample. The method includes amplifying a target sequence, which includes the target nucleotide and one or more methylated control sequence nucleotides, using terminator-coupled linear amplification reaction that includes a terminator for cytosine (or guanine, when analyzing the opposite strand). The abundance of the fluorescent peak corresponding to each extension product can be measured by quantifying the area below the peak and/or the height of the peak. The abundance of each extension product is indicative of the relative abundance of the methylation status of the particular CpG in the target sequence. The observed abundance of each extension product is compared to the expected relative abundance in a reference standard. The reference standard is generated by determining the relative abundance of extension products produced by the terminator-coupled linear amplification reaction as used to analyze multiple control samples, each of which includes a different (i) known fraction or percent (M %) of the polynucleotide target sequence having the particular target nucleotide fully methylated and (ii) known fraction or percent (100%-M %) of the polynucleotide target sequence having the particular target nucleotide fully non-methylated. The relative abundance of the extension products in the reference standard can be used to estimate the relative abundance of methylated and unmethylated cytosines in a sample.

Another method for analyzing the percent or extent of methylation of a particular target nucleotide (e.g. a target cytosine in a genomic CpG dinucleotide) in a test sample includes amplifying a target sequence (with the target nucleotide and one or more methylated control sequence nucleotides) in a way that also copies the methylation pattern of the target sequence, analyzing the amplified target sequence by terminator-coupled linear amplification to generate one or more extension products that indicate the methylation status of the one or more target nucleotides, detecting the amount of each extension product that correlates with the methylation status each target nucleotide, and comparing the quantified amount of each extension product to the amount of a corresponding extension product in a reference standard. The reference standard can be generated by amplifying and copying the methylation pattern (using the same method as for the test sample) of the target sequence in multiple control samples. Each control sample includes a different (i) known fraction or percent (M %) of the polynucleotide target sequence having the particular target nucleotide fully methylated and (ii) known fraction or percent (100%-M %) of the polynucleotide target sequence having the particular target nucleotide fully non-methylated. The amplified products are analyzed by terminator-coupled linear amplification to generate one or more extension products that indicate the methylation status of the particular target nucleotide, and the amount of each extension product is included in the reference standard. Since the amount of each extension product in the reference standard correlates with a particular fraction or percent of methylated (M %) and unmethylated target nucleotide (100-M %), the amount of each extension product indicating the methylation status of a target nucleotide in the test sample can be compared to the corresponding closest amounts in the reference standard to determine the particular fraction or percent of methylated (M %) and unmethylated target nucleotide (100-M %) in the test sample.

The amount of each extension product for a particular target nucleotide in a reference standard preferably reflects the average amount of extension products for the particular target nucleotide generated from multiple control samples having the same fraction or percent of methylated (M %) and unmethylated target nucleotide (100-M %).

The methods of the invention also can be used to evaluate the methylation density of a target sequence in a sample. Generally, the methods for evaluating methylation density include methylating one or more control sequence nucleotides in the target sequence and evaluating the methylation status of multiple target nucleotides in the target sequence according to any suitable method disclosed herein. Preferred methods for evaluating the methylation status of multiple target nucleotides, for example target cytosines in CpG islands, include terminator-coupled linear amplification. The number of methylated target nucleotides in the target sequence indicates the methylation density of the target sequence.

Fluorescent dideoxy sequencing can also be used (i.e., instead of terminator-coupled linear amplification) to generate the extension products used in methods described herein for (a) analyzing the percent or extent of methylation a target nucleotide and/or (b) evaluating the methylation density of a target sequence in a sample. When using sequencing in the aforementioned methods, the same sequencing conditions are also used to generate the appropriate reference standards.

Additionally, in this regard, the inventors have observed that introducing internal control sequence nucleotides can improve the quality of sequencing information obtained from bisulfite-treated templates. This improvement may be due, at least in part, to the preservation of cytosines (or guanines on the opposite strand) and, thus, better representation of all four nucleotides normally amplified by polymerases used for DNA sequencing.

The methods of the invention can be used to evaluate the methylation status of a CpG island having a methylation status that is associated with a disease state such as cancer. For example, the methods of the invention can be used to evaluate the methylation status of one or more CpG islands associated with prostate cancer, which reportedly include CpG islands associated with glutathione S-transferase P1 (GSTP1), glutathione peroxidase 3 (GPX3), glutathione S-transferase M1 (GSTM1), glutathione S-transferase M4 (GSTM4), Cub and Sushi multiple domains1 (CSMD1), tumor necrosis factor receptor superfamily member 10A (TNFRSF10A), tumor necrosis factor receptor superfamily member 10B (TNFRSF10B), tumor necrosis factor receptor superfamily member 10C (TNFRSF10C), tumor necrosis factor receptor superfamily 10D (TNFRSF10D), secreted frizzled-related protein 1 (SFRP1), secreted frizzled-related protein 2 (SFRP2), dickkopf homolog 3 (DKK3), prostaglandin-endoperoxide synthase 2 (PTGS2), cyclin-dependent kinase inhibitor 1C (CDKN1C/p57), Ras association (Ra1GDS/AF-6) domain family 1 (RASSF1), and G-protein coupled receptor 62 (GPR62), neuregulin cell-surface ligand (NRG1), adrenergic B3 receptor (ADRB3), glycosylphosphatidylinositol cell-surface receptor (GFRA2), kinesin family member 13B (KIF13B), RET proto-oncogene (RET), G-protein-coupled protein receptor 147 (GPR147), neurogenin 3 transcription factor (NEUROG3), paladin (predicted protein tyrosine phosphatase) (PALD), methyltransferase family member 1 (HEMK1), fibroblast growth factor 4 oncogene (FGF4), 5-hydroxytryptamine (serotonin) receptor 1A (HTR1A), ring finger protein 180 (LOG 285671 or RNF180), EGFR-co-amplified and overexpressed (DKFZP564K0822 or ECOP), zinc finger protein 596 (ZNF596), similar to 7 transmembrane helix receptor (LOC441320), L-threonine dehydrogenase (TDH), hypothetical protein FLJ36980 (FLJ36980), fibroblast growth factor receptor 20 (FGF20), EF-hand domain family member 2A (LOC286097 or EFHA2), N-acylsphingosine amidohydrolase (acid ceraminase) 1 (ASAH1), nodal homolog (TGF-β signaling pathway) (NODAL), hypothetical protein similar to zinc finger protein 532 (LOC399783), transcription factor LIM homeodomain (ISL2) Kinesin family member C2 (KIFC2), chromosome 20 open reading frame 23 (Kinesin-like motor protein) (C20orf23), GDNF family receptor alpha 1 (GFRA1), Glutathione peroxidase 7 (GPX7), Dickkopf homolog 2 (DKK2), netrin 1 (NTN1), matrix metallopeptidase 9 (MMP9), tumor necrosis factor superfamily member 11 (TN-FSF11), ras homolog gene family member D (RHOD), leucine rich repeat containing 49 (LRRC49), Kinesin family member C2 (KIFC2), chromosome 20 open reading frame 23 (Kinesin-like motor protein) (C20orf23), GDNF family receptor alpha 1 (GFRA1), Dickkopf homolog 2 (DKK2), netrin 1 (NTN1), Ras association (Ra1GDS/AF-6) domain family 5 (RASSF5), and HtrA serine peptidase 4 (HTRA4).

The methods of the invention also can be used to evaluate CpG islands associated with other types of cancer. Other types of cancer include leukemia (e.g., lymphoblastic, myeloid, hairy cell), adrenocortical carcinoma, anal cancer, appendix cancer, astrocytoma, basal cell carcinoma, extrahepatic bile duct cancer, bladder cancer, bone cancer, brain cancer, gliomas, breast cancer, bronchial adenomas, carcinoid tumors, cervical cancer, myeloproliferative disorders, colon cancer, endometrial cancer, esophageal cancer, eye cancer, gallbladder cancer, stomach cancer, gastrointestinal tumors, head and neck cancer, liver cancer, pancreatic cancer, lymphomas (e.g., Hodgkin's, Non-Hodgkin's, Burkitt's, T-cell, central nervous system, and AIDS-related), sarcomas, kidney cancer, laryngeal cancer, lip and oral cavity cancer, liver cancer, lung cancer, macroglobulinemia, melanoma, Merkel cell carcinoma, mesothelioma, myeloproliferative disorders, nasal and paranasal sinus cancer, nasopharyngeal cancer, neuroblastoma, ovarian cancer, pancreatic cancer, parathyroid cancer, penile cancer, pharyngeal cancer, pheochromocytoma, pituitary tumor, rectal cancer, kidney cancer, salivary gland cancer, skin cancer (non-melanoma), testicular cancer, throat cancer, thyroid cancer, trophoblastic tumor ureter and renal pelvis cancer, urethral cancer, uterine cancer, vaginal cancer, and vulvar cancer.

Inasmuch as they avoid depleting sample DNA, the methods of the invention can be for used to evaluate the methylation status of multiple target sequences (or methylation markers) in samples that include relatively small amounts of DNA, e.g., the samples described herein, supra. The methods of the invention can be used to evaluate the methylation status of 2 or more, 3 or more, 4 or more, 5 or more, 6 or more, 7 or more, 8 or more, 9 or more, 10 or more, 11 or more, 12 or more, 13 or more, or 15 or more target sequences in a sample that includes a relatively small amount of genomic DNA. Thus, for example, the methods of the invention can be used to evaluate circulating genomic DNA in urine for the methylation status of multiple (e.g., 2 or more, 3 or more, 4 or more, 5 or more, 6 or more, 7 or more, 8 or more, 9 or more, 10 or more, 11 or more, 12 or more, 13 or more, or 15 or more) CpG islands associated with prostate cancer.

When analyzing multiple markers, the methods of the invention can include techniques such as multiplex PCR, nested PCR and the use of modified or degenerate primers. For example, primers can be degenerate at the position corresponding to one or more cytosine within a CpG dinucleotide. Such primers can be used to maximize the amplification from all templates present within a sample or to maximize the amplification of all methylated templates within the sample.

Primers can include a tail sequence at their 5' end that can be used as a primer annealing site for terminator-coupled linear amplification. Such tail sequences can be used to normalize the yield from terminator-coupled linear amplification reactions. Tail sequences can include, for example, sequences that anneal to commonly used sequencing primers such as M13 forward or reverse primers.

The methods of the invention are also suitable for evaluating the methylation density of multiple (e.g., 2 or more, 3 or more, 4 or more, 5 or more, 6 or more, 7 or more, 8 or more, 9 or more, 10 or more, 11 or more, 12 or more, 13 or more, or 15 or more) target sequences in samples that include more than a relatively small amount of DNA.

Generally, the methods of the invention include introducing one or more internal control sequence nucleotides by treating a sample to be analyzed (e.g, a tissue sample, a bodily fluid sample, purified DNA, and/or amplified DNA) with a methylase that preferentially methylates one or more control sequence nucleotides in the target sequence of interest. In addition to the advantages identified above, the internal control also provides direct information about the reactions that include the sample polynucleotide(s) whose methylation status is being probed.

Such direct information is not available using methods that include a separate, parallel control reaction. For example, WO 2007/033834 describes a two-step PCR-based reaction for identifying methylated CpG residues in genomic DNA. WO 2007/033834 also describes making a positive control by treating a separate aliquot of the genomic DNA with SssI methylase (or M.SssI), which methylates cytosines in CpG dinucleotides. Presumably, the disclosed method includes comparing the product of the PCR reaction that includes untreated genomic DNA with a separate PCR reaction that includes the positive control. In this method, the positive control reaction provides only indirect information about the reaction that includes the untreated genomic DNA. Thus, if the reaction that includes untreated genomic DNA does not produce the expected PCR product indicating the presence of methylated CpG dinucleotides, and the control reaction does produce the expected PCR product, the positive control does not provide any information about whether the PCR reaction that includes the untreated genomic DNA failed because, for example, there was insufficient genomic DNA template or whether the PCR reaction failed for other reasons.

In the methods of the present invention, the control nucleotide is found on the same polynucleotide as the target nucleotide, and thus both the control and target nucleotide are present in the same reaction. Thus, for example, in the methods described herein, the assaying for methylation of a target nucleotide can include assaying for methylated cytosines using only a dideoxycytosine terminator. When the assaying produces a negative result (i.e., no output) for a target cytosine nucleotide, a positive result for the methylated cytosine control nucleotide will indicate that the assay conditions were adequate and that the negative result for the target cytosine was not due to insufficient sample polynucleotide, failure of polynucleotide purification, or failure of target sequence amplification. Thus, the internal controls of the invention can provide a greater confidence in the results of a methylation assay than methods including only an external, separate control.

In the methods of the invention, a negative result for both the target nucleotide and the control nucleotide can indicate an insufficient amount of polynucleotide in the sample, failure to adequately purify the polynucleotide, failure to adequately amplify the polynucleotide, or some other technical defect in the reagents or equipment used to assay methylation status. Unlike prior methods, however, the methods of the invention do not require separate external control reaction to verify that the assay was defective.

The following example further illustrates the invention but, of course, should not be construed as in any way limiting its scope.

Example 1

This example demonstrates the analysis of the methylation pattern of two CpG islands (target sequences) associated with the GPX7 and GPR147 genes from DNA samples recovered from a prostate tumor and human lymphoblastoid cell lines.

For reference, target sequences in the CpG islands associated with the GPX7 and GPR147 genes are provided. The following represent genomic DNA target sequences prior to bisulfite treatment modification.

```
GPX7 CpG island:
                                            (SEQ ID NO: 1)
AGAAACTGAGGTCGGAGTGGGGGCGTGACCAGGCCAGCCTAAGGCCGCT

GCACTAATGAGAAGCTGAGCTCTCAGATTTTTGCCTCCCTGTCCCTGCC
```

-continued

AAGTCGCTGTTTCCTGGGACAAGAGGGAGCCTCACTGAAACGAACTCCG

GTCTCAGGGGACAGAATCCTGAAACCCTGGCTCTGGGGTCCGGGGCAGG

GGTGCGCTGCCTCAGGACAGACGGTGAAACTGAGGTCCAGAGCCGGACA

TCCACCGCCTGCGGAGGGAACGAGAACGCGGCGCGTCCTGCCTTGCGGG

CCGAGCGGCGCCAGAGCCGCCTCCTCCCGCCCCCGCGCTAGATCCCC

CGCCCCGTCTTTGCCCTCGCGACGCCGCCACCTCCGGAACAAGCCATGG

CTGGCGGCGACGGTGGCAGCGGCGTGGTGCTCCTGTGGGCTGCGGCCTG

CGCGCAGCAGGAGCAGGACTTCTACGACTTCAAGGCGGTCAACATCCGG

GGCAAACTGGTGTCGCTGGAGAAGTACCGCGGATCGGTGAGTGCGCGGG

G.

GPR147 CpG island:
(SEQ ID NO: 2)
ACCCTTTCCGCGAGAAGCTGACCCTGCGGAAGGCGCTCGTCACCATCGC

CGTCATCTGGGCCCTGGCGCTGCTCATCATGTGTCCCTCGGCCGTCACG

CTGACCGTCACCCGTGAGGAGCACCACTTCATGGTGGACGCCCGCAACC

GCTCCTACCCGCTCTACTCCTGCTGGGAGGCCTGGCCCGAGAAGGGCAT

GCGCAGGGTCTACACCACTGTGCTCTTCTCGCACATCTACCTGGCGCCG

CTGGCGCTCATCGTGGTCATGTACGCCCGCATCGCGCGCAAGCTCTGCC

AGGCCCCGGGCCCGGCCCCCGGGGGCGAGGAGGCTGCGGACCCGCGAGC

ATCGCGGCGCAGAGCGCGCGTGGTGCACATGCTGGTCATGGTGGCGCTG

TTCTTCACGCTGTCCTGGCTGCCGCTCT.

DNA is extracted from paraffin-embedded prostate tumor tissues after microdissection. Paraffin is removed by extraction twice with xylene. DNA is extracted by extended proteinase K digestion in extraction buffer (25 mM tris pH 8.0, 0.5% SDS, 5 mM EDTA, 100 mM NaCl) supplemented with 50 µg/ml of proteinase K for 72 hours, followed by phenol/chloroform extraction and precipitation. The DNA is resuspended in TE8 buffer (10 mM Tris, pH 8.0, 1 mM EDTA). The concentration is determined by agarose gel electrophoresis and comparison with a concentration standard. The DNA is diluted to a final concentration of 100 ng/ul in TE8.

DNA is isolated from lymphoblastoid cell lines as described for the prostate tumor DNA extraction except that the xylene extraction step was omitted.

1 µg of genomic DNA is methylated using MspI methylase (New England Biolabs ("NEB"), Beverly Mass.) according to manufacturer's recommendations in 50 µl of 1× buffer (50 mM Tris HCL, 10 mM NaCl, 1 mM EDTA, and 0.5 mM 2-mercaptoethanol, pH 7.5 at 25° C.) supplemented with 80 µM S-adenosylmethionine. The DNA is then extracted with phenol/chloroform, precipitated with ethanol, and resuspended in TE8. The DNA is then subjected to a second methylation reaction with HaeIII methylase (NEB) according to manufacturer's recommendations in 50 µl of 1× buffer (50 mM Tris HCL, 50 mM NaCl, and 10 mM DTT, pH 8.5 at 25° C.). Following methylation, the DNA is denatured by incubation in a final concentration of 0.2 M NaOH at 40° C. for 10 minutes.

To generate a fully methylated (external) control DNA, 1 µg of lymphoblastoid genomic DNA is methylated with SssI methylase (NEB) according to manufacturer's recommendations. The DNA is then subjected to treatment with MspI and HaeIII methylases as described above.

Bisulfite treatment is performed in accordance with a modification of the methods of Frommer et al. in *Proc. Nat'l Acad. Sci. USA,* 89: 1827-1831 (1992). 550 µl of a freshly prepared 3M sodium bisulfite solution (pH 5.0 with 10 N NaOH) and 5 µl of 400 mM hydroquinone are added to the denatured DNA. The DNA is incubated in a PCR machine for 8 cycles of 94° C. for 5 minutes, and 55° C. for 120 minutes.

Following bisulfite treatment, DNA is purified using a glass milk purification procedure according to the manufacturer's protocol (QIAEX II™, QIAGEN). The DNA is eluted in 100 µl of TE8. One-tenth volume of 3M NaOH is added and the DNA is incubated at room temperature for 5 minutes. The DNA is precipitated by the addition of 0.4 volume of 5 M ammonium acetate, 5 µg of linear acrylamide (carrier), and 3 volumes of ethanol. The DNA is resuspended in 40 µl of TE8, and stored frozen at −20° C.

1 µl of the methylated bisulfite-treated DNA is amplified using primers NF1 and NR1 for the GPX7 and GPR147CpG islands. The primers, designed to anneal to SEQ ID NO:1 or SEQ ID NO:2 following bisulfite-treatment, are set forth in Table 2.

TABLE 2

| Primer Name | Primer Sequence |
| --- | --- |
| GPX7-NF1 | GTTGTTTTTTGGGATAAGAGGGAG (SEQ ID NO: 3) |
| GPX7-NR1 | AATCRTAAAAATCCTACTCCTACTAC (SEQ ID NO: 4) |
| GPX7-NF2 | *GGATAGAATTTTGAAATTTTGGTT (SEQ ID NO: 5) |
| GPR147-NF1 | GAGAAGTTGATTTTGYGGAAGG (SEQ ID NO: 6) |
| GPR147-NR1 | CCACCATAACCAACATATACACC (SEQ ID NO: 7) |
| GPR147-NF2 | *GGTTTTGGYGTTGTTTATTATGTG (SEQ ID NO: 8) |

*indicates the presence of a fluorescent label in the corresponding primer. GPX7-NF2 is labeled with 6-FAM fluorescent dye, and GPR147-NF2 is labeled with VIC ™ fluorescent dye (Applied Biosystems).

All PCR reactions are performed for 40 cycles of 95° C. for 15 seconds, 58° C. for 20 seconds, and 72° C. for 20 seconds. Each reaction was carried out in 30 µA volume of 1× PLATINUM™ Taq PCR buffer (20 mM Tris-HCL, 50 mM KCl, 1.5 mM MgCl$_2$, pH 8.4 at 25° C.) (Invitrogen, Carlsbad, Calif.), 0.25 mM dNTPs, 12.5 picomoles of each primer, 0.5 units of PLATINUM™ Taq enzyme (Invitrogen) and 1 µl of the methylated bisulfite treated DNA. The amplification products are separated on an 8% acrylamide gel, and eluted into 100 µl of extraction buffer (10 mM Tris HCl, 1 mM EDTA, 100 mM NaCl, pH 8.0). Following ethanol precipitation, the DNA is resuspended in 20 µl of TE8.

10 nanograms of the PCR amplification product are subjected to terminator-coupled linear amplification using 1.5 picomoles of the fluorescently labeled NF2 primer corresponding to each amplicon. The amplification reaction was performed in 1× VENT™ (exo-) DNA polymerase buffer (NEB), 30 µM dATP, 37 µM dCTP, 100 µM dGTP, 100 µM dTTP, 480 µM ddCTP and 2 units of VENT™ (exo-) DNA polymerase (NEB). PCR reactions are performed in an Eppendorf MASTERCYCLER™ for 30 cycles of 95° C. for 15 seconds, 58° C. for 30 seconds, and 72° C. for 30 seconds. Following amplification, the reactions are pooled into a single tube and purified using CENTRI-SEP™ columns (Applied Biosystems) according to the manufacturer's protocols. One microliter of GENESCAN™-500 LIZ standard (Applied Biosystems) is added to the purified fragments and the DNA separated using the ABI Prism 310 Genetic Analyzer (Applied Biosystems) according to manufacturer's instructions. The data is analyzed using the GENESCAN™ and the GENEMAPPER™ software (Applied Biosystems).

Terminator-coupled amplification of the GPX7 target sequence from the lymphocyte DNA (untreated with SssI methylase) results in 5 detectable fluorescence peaks corresponding to amplification products of 32, 84, 139, 222, and 283 bp in length. These 5 amplification products terminate at sequence positions corresponding to cytosine residues (i.e., internal control sequence nucleotides) methylated by MspI and HaeIII methylases. For the tumor DNA, up to 34 additional peaks are observed corresponding to amplification products of 33, 46, 63, 96, 102, 111, 117, 119, 122, 124, 136, 141, 145, 148, 157, 167, 174, 176, 189, 194, 206, 208, 211, 214, 223, 241, 244, 247, 256, 259, 280, 287, 289, and 311 bp in length. Each of these 34 products terminates at a sequence position corresponding to a methylated CpG dinucleotide. For SssI-methylated DNA, all 39 peaks (5 control sequence nucleotides+34 CpG dinucleotides) are detectable.

Terminator-coupled amplification of the GPR147 target sequence from the lymphocyte DNA (untreated with SssI methylase) results in 9 detectable fluorescence peaks corresponding to amplification products of 33, 120, 125, 240, 242, 247, 248, 251, and 255 bp in length. These 9 amplification products terminate at sequence positions corresponding to cytosine residues (i.e., internal control sequence nucleotides) methylated by MspI and HaeIII methylases. For the tumor DNA, up to 34 additional peaks are detected corresponding to amplification products of 30, 34, 39, 46, 53, 79, 83, 89, 99, 127, 140, 168, 183, 186, 192, 199, 211, 215, 220, 222, 224, 243, 249, 256, 262, 273, 279, 281, 288, 290, 293, 300, 302, and 304 bp in length. Each of these 34 products terminates at a sequence position corresponding to a methylated CpG dinucleotide. For the SssI methylated DNA, all 43 peaks (9 control sequence nucleotides+34 CpG dinucleotides) are detectable.

This example shows that methylases with recognition sites other than CpG dinucleotides can be used to add internal control sequence nucleotides to genomic DNA samples that include CpG island markers of interest. In this example, the assay provides a positive signal only for methylated or protected cytosine residues. Without the one or more internal control nucleotides, it would be unclear if an absence of expected amplification products corresponding to particular methylated CpG markers of interest in the lymphocyte DNA is due to (a) an absence of methylation at the CpG markers, (b) an insufficient amount genomic DNA that includes the target sequence, or (c) another technical failure. The control sequence nucleotides verify that there was a sufficient amount of starting DNA and that the multiple reactions in the assay are technically sound. Moreover, the verification does not require a separate external control reaction.

Example 2

This example demonstrates the use of HaeIII methylase to generate an internal control from unmethylated and fully methylated DNA. This example also demonstrates the use of terminator-coupled linear amplification to analyze the methylation pattern of the GSTP1 promoter CpG island.

The following CpG island target sequence (prior to bisulfite treatment modification) associated with GSTP1 is provided for reference.

GSTP1 CPG island:
(SEQ ID NO: 9)
TCCCTAGGCCCCGCTGGGGACCTGGGAAAGAGGGAAAGGCTTCCCCGGC

CAGCTGCGCGGCGACTCCGGGGACTCCAGGGCGCCCCTCTGCGGCCGAC

GCCCGGGGTGCAGCGGCCGCCGGGGCTGGGGCCGGCGGGAGTCCGCGGG

ACCCTCCAGAAGAGCGGCCGGCGCCGTGACTCAGCACTGGGGCGGAGCG

GGGCGGGACCACCCTTATAAGGCTCGGAGGCCGCGAGGCCTTCGCTGGA

GTTTCGCCGCCGCAGTCTTCGCCACCAGTGAGTACGCGCGGCCCGCGTC

CCCGGGGATGGGGCTCAGAGCTCCCAGCATGGGGCCAACCCGCAGCATC

AGGCCCGGGCTCCCGGCAGGGCTCCTCGCCCACCTCGAGACCCGGGACG

GGGGCCTAGGGGACCCAGGACGTCCCCAGTGCCGTTAGCGGCTTTCAGG

GGGCCCGGA.

1 microgram of lymphoblastoid cell line genomic DNA was methylated using HaeIII methylase (NEB) for 16 hours at 37° C. in 50 μl of 1× buffer (50 mM Tris HCL, 50 mM NaCl, and 10 mM DTT, pH 8.5 at 25° C.) supplemented with 80 μM S-adenosylmethionine to generate a DNA control, which is unmethylated at the GSTP1 locus except for methylation introduced in vitro at HaeIII enzyme recognition sites. Fully methylated control was generated by methylating 1 microgram of lymphocyte genomic DNA with a combination of 2 units each of HaeIII and SssI methylases in 50 μl of NEB buffer 2 (10 mM Tris pH 7.9 at 25° C., 50 mM NaCl, 10 mM MgCl$_2$, and 1 mM DTT) supplemented with 80 μM S-adenosylmethionine for 16 hours at 37° C. Following the methylation reaction, the DNA was denatured and subjected to bisulfite treatment as described in Example 1.

All PCR reactions were performed for 42 cycles of 95° C. for 15 seconds, 58° C. for 20 seconds, and 72° C. for 20 seconds. Each reaction was carried out in 30 μl volume of 1× PLATINUM™ Taq PCR buffer, 0.25 mM dNTPS, 25 pmoles of each primer (GSTP1 NF1 and GSTP1 NR1), 0.5 units of PLATINUM™ Taq polymerase, and 1 μl of the bisulfite treated DNA. Amplification products were separated on an 8% acrylamide gel, and eluted into 100 μl of TE8 buffer overnight on a shaking platform. Supernatant containing the DNA was recovered following centrifugation, and the DNA was used directly without further manipulations.

10 μl of the recovered amplification product was subjected to terminator-coupled linear amplification using 1.5 picomoles of the fluorescently labeled primer corresponding to each methylated or unmethylated template (GSTPI_BMF1F, GSTPI_BUF1F, respectively). The amplification reaction was performed in 1× ThermoPol buffer (NEB) (20 mM Tris-HCl, 10 mM (NH$_4$)$_2$SO$_4$, 10 mM KCl, 2 mM MgSO$_4$, pH 8.8 at 25° C.), 100 μM of dNTPs, 40 μM of acy-CTP (NEB), 0.2 units of thermostable inorganic pyrophosphatase (NEB), and 0.5 units of THERMINATOR™ II DNA polymerase (NEB). Reactions were performed in an Eppendorf MASTERCYCLER™ for 30 cycles of 95° C. for 15 seconds, 58° C. for 20 seconds for GSTPI_BMF1F primer or 50° C. for 20 seconds for GSTPI_BUF1F primer, and 72° C. for 1 minute. Following amplification, 3 μl of the amplification reaction was diluted in 26 μl formamide. 1 μl of GENESCAN™-500 LIZ standard (Applied Biosystems) was added and the DNA separated using the ABI Prism 310 Genetic Analyzer (Applied Biosystems) according to manufacturer's instructions. The data was analyzed using the GeneMapper software (Applied Biosystems). Primers, which are designed to anneal to bisulfite-treated template, are set forth in Table 3.

TABLE 3

| Primer Name | Primer Sequence |
|---|---|
| GSTPI_NF1 | GGATTTGGGAAAGAGGGAAAGGTTT (SEQ ID NO: 10) |
| GSTPI_NR1 | ACTAAAAACTCTAAACCCCATCCC (SEQ ID NO: 11) |
| GSTPI_BMF1F | *GCGATTTCGGGGATTTTAGGGCGTT (SEQ ID NO: 12) |
| GSTPI_BUF1F | *GTGTGGTGATTTTGGGGATTTTAGG (SEQ ID NO: 13) |

*indicates the presence of a fluorescent label in the corresponding primer. GSTPI_BMF1F (for methylated template) was labeled with 6-FAM fluorescent dye, and GSTPI_BUF1F (for unmethylated template) was labeled with VIC™ fluorescent dye (Applied Biosystems).

Terminator-coupled amplification of unmethylated template resulted in 7 fluorescent peaks corresponding to in vitro HaeIII methylation sites. The 7 peaks correspond to amplification products of 40, 61, 76, 111, 173, 181, and 233 bp in length.

Terminator-coupled amplification of fully methylated DNA also resulted in 7 fluorescent peaks corresponding to in vitro HaeIII methylation sites. Because the template annealing site for GSTPI_BMF1F is shifted by 5 bp relative to GSTPI_BUF1F, the 7 fluorescent peaks correspond to amplification products of 35, 56, 71, 106, 168, 176, and 228 bp. Additionally, terminator-coupled amplification of the fully methylated template resulted in up to 31 additional peaks, which correspond to amplification products of 32, 36, 39, 43, 53, 57, 60, 72, 75, 83, 85, 103, 107, 110, 113, 131, 136, 141, 162, 169, 171, 180, 191, 194, 197, 206, 221, 223, 225, 232, and 238 bp in length. Each of these amplification products terminated at a sequence position corresponding to a methylated CpG dinucleotide site. Peaks below 50 bp in length were disregarded because of their proximity to the primer peak.

Example 3

This example demonstrates the use of degenerate primers with a 5' tail sequence in terminator-coupled linear amplification and the use of HaeIII methylase to generate an internal control. This example also demonstrates a method of obtaining information that can be used to indicate the fraction or percentage of polynucleotides comprising a methylated target sequence in a sample.

DNA was extracted from a lymphoblastoid cell line and from 2 paraffin-embedded prostate tumor tissues after microdissection as described in Example 1. DNA was methylated using HaeIII methylase and subjected to bisulfite treatment as also described in Example 1. Fully methylated DNA control was generated as described in Example 2.

PCR reactions were performed generally as described in Example 2, except that degenerate primers M13GSTPI_BDF1 and BDR1b were used and reactions included 42 cycles of 95° C. for 15 seconds, 60° C. for 20 seconds, and 72° C. for 20 seconds. PCR amplification products were separated on an 8% acrylamide gel, and eluted into 100 µl of TE8 buffer overnight on a shaking platform. The supernatant containing the DNA was recovered following centrifugation and the DNA was used directly without further manipulations. M13GSTPI_BDF1 and BDR1b primers, which are designed to anneal to bisulfite-treated template, are set forth in Table 4.

TABLE 4

| Primer Name | Primer Sequence |
|---|---|
| M13GSTPI_BDF1 | CAGGAAACAGCTATGACYGGYGATTTYGGG GATTTTAGGGYGT (SEQ ID NO: 14) |
| BDR1b | ACTAAAAACTCTAAACCCCATCCC (SEQ ID NO: 15) |

10 µl of recovered DNA was subjected to terminator-coupled linear amplification using fluorescently labeled M13R primer ddCTP termination mix (from BIGDYE™ Primer Cycle Sequencing Ready Reaction M13REV, Applied Biosystems) supplemented with 0.5 µM ddCTP (USB Biochemicals, Cleveland, Ohio). The linear amplification reaction included 30 cycles of 94° C. for 15 seconds, 50° C. for 20 seconds, and 60° C. for 1 minute. Following amplification, 2 µl of the amplification reaction was diluted in 27 µl of formamide without further manipulation. 1 µl of GENESCAN™-500 LIZ standard (Applied Biosystems) was added, and the DNA separated using the ABI Prism 310 Genetic Analyzer (Applied Biosystems) according to manufacturer's instructions. The data was analyzed using the GeneMapper software (Applied Biosystems).

Terminator-coupled amplification of fully methylated DNA resulted in fluorescent peaks corresponding to in vitro HaeIII methylation sites. Peaks corresponded to amplification products of 54, 75, 90, 125, 187, 195 bp in length. Additionally, terminator-coupled amplification of fully methylated and tumor samples resulted in up to 25 additional peaks, which correspond to amplification products of 51, 55, 58, 62, 72, 76, 79, 91, 94, 102, 104, 122, 126, 129, 132, 150, 155, 160, 181, 188, 190, 199, 210, 213, 216 bp in length. Each of these amplification products terminated at a sequence position corresponding to a methylated CpG dinucleotide site.

The heights and the areas below the fluorescent peaks corresponding to the CpG dinucleotide sites in tumor samples ranged from between 25% to less than 10% of those corresponding to the CpG dinucleotide sites in the fully methylated control. The heights and the areas below the fluorescent peaks corresponding to the CpG dinucleotide sites in tumor samples also were about 10% of the height and areas of the peaks corresponding to HaeIII methylated cytosines within the same tumor sample. These data provide information that can be used to determine the fraction of a methylated CpG dinucleotide site in the sample.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for analyzing the methylation status of a target sequence in a sample with an internal control for detecting the presence of the target sequence, the method comprising:
   (a) providing a sample that includes DNA, wherein the sample DNA includes a target sequence;
   (b) optionally, purifying the DNA from the sample to thereby produce purified DNA;
   (c) optionally, amplifying the DNA and simultaneously copying the methylation pattern of the DNA to thereby produce amplified DNA;
   (d) treating the sample DNA, purified DNA, or amplified DNA with a methylase that preferentially methylates at one or more control sequence nucleotides in the target sequence, wherein (i) the target sequence and the one or more control sequence nucleotides are present in the DNA before the DNA is optionally amplified, (ii) the methylase preferentially methylates cytosines other than cytosines in CpG dinucleotides, and (iii) the methylase has a recognition sequence that includes a GpC dinucleotide; and
   (e) assaying the sample, purified DNA, or amplified DNA for the methylation status of (i') the one or more control sequence nucleotides and (ii') one or more CpG dinucleotides in the target sequence;
   wherein (a') methylation at the one or more control sequence nucleotides indicates the presence of the target sequence in the sample before the DNA from the sample is optionally amplified, and the presence or absence of methylation at the one or more CpG dinucleotides indicates the presence or absence, respectively, of methylation at the corresponding dinucleotides in the sample, or (b') absence of methylation at the one or more control sequence nucleotides indicates the absence of the target sequence in the sample, purified DNA, or amplified DNA and/or a technical failure.

2. The method of claim 1, wherein (e) comprises using terminator-coupled linear amplification suitable for generating extension products that indicate (i') the methylation status of the one or more control sequence nucleotides in the treated sample, purified DNA, or amplified DNA and (ii') the methylation status of one or more CpG dinucleotides in the target sequence; and wherein (a') methylation at the one or more control sequence nucleotides indicates the presence of the target sequence in the sample, and the presence or absence of methylation at the one or more CpG dinucleotides indicates the presence or absence, respectively, of methylation at the corresponding dinucleotides in the sample, or (b') absence of methylation at the one or more control sequence nucleotides indicates the absence of the target sequence in the sample, purified DNA, or amplified DNA and/or failure of the terminator-coupled linear amplification reaction.

3. The method of claim 1, wherein the sample is a bodily fluid selected from the group consisting of blood, blood plasma, blood serum, urine, sputum, ejaculate, semen, tears, sweat, saliva, lymph fluid, bronchial lavage, pleural effusion, peritoneal fluid, meningeal fluid, amniotic fluid, glandular fluid, fine needle aspirates, nipple aspirate fluid, spinal fluid, conjunctival fluid, vaginal fluid, duodenal juice, pancreatic juice, pancreatic tissue bile, and cerebrospinal fluid.

4. The method of claim 1, wherein the methylase preferentially methylates cytosine residues within a recognition sequence that comprises the sequence AGCT, GGCC, GCNGC, or GCGC.

5. The method of claim 1, wherein the target sequence includes at least a portion of a CpG island having a methylation status that is associated with prostate cancer.

6. The method of claim 5, wherein the CpG island is associated with a gene selected from the group consisting of GSTP1, CSMD1, TNFRSF10A, TNFRSF10B, INFRSF10C, TNFRSF10D, SFRP1, SFRP2, DKK3, PTGS2, CDKN1C/p57, RASSF5, GPR62, KIF13B, NEUROG3, PALD, HEMK1, FGF20, NODAL, KIFC2, and GPX7.

7. The method of claim 1, wherein the sample includes less than 10 nanograms of DNA.

8. The method of claim 7, wherein the sample includes fewer than 150 contiguous nucleotides that include the target sequence.

9. The method of claim 7, wherein the sample is urine and the target sequence includes at least a portion of a CpG island having a methylation status that is associated with prostate cancer.

10. The method of claim 9, wherein the CpG island is associated with a gene selected from the group consisting of GSTP1, CSMD1, TNFRSF10A, TNFRSF10B, TNFRSF10C, TNFRSF10D, SFRP1, SFRP2, DKK3, PTGS2, CDKN1C/p57, RASSF5, GPR62, KIF13B, NEUROG3, PALD, HEMK1, FGF20, NODAL, KIFC2, and GPX7.

11. The method of claim 10, wherein the methylase preferentially methylates cytosine residues within a recognition sequence that comprises the sequence AGCT, GGCC, GCNGC, or GCGC.

12. The method of claim 1, wherein (e) assaying the sample, purified DNA, or amplified DNA for the methylation status of (i) the one or more control sequence nucleotides and (ii) the one or more CpG dinucleotides in the target sequence comprises digesting the sample, purified DNA, or amplified DNA with a sequence specific restriction endonuclease.

13. The method of claim 1, wherein (e) assaying the sample, purified DNA, or amplified DNA for the methylation status of (i) the one or more control sequence nucleotides and (ii) the one or more CpG dinucleotides in the target sequence comprises using methylation-sensitive single nucleotide primer extension, fluorescent-based real time PCR, headloop suppression PCR, ligation-mediated amplification, microarray analysis, or mass spectrometry.

14. A method for evaluating the density of DNA methylation in a target sequence with an internal control for detecting the presence or absence of the target sequence, the method comprising:

(a) providing a sample that includes DNA, wherein the sample DNA includes a target sequence;
(b) optionally, purifying the DNA to thereby produce purified DNA;
(c) optionally, amplifying the DNA and simultaneously copying the methylation pattern of the DNA to thereby produce amplified DNA;
(d) treating the sample DNA, purified DNA, or amplified DNA with a methylase that preferentially methylates at one or more control sequence nucleotides in the target sequence, wherein (i) the target sequence and the control sequence nucleotide are present in the DNA before the DNA is optionally amplified, (ii) the methylase preferentially methylates cytosines other than cytosines in CpG dinucleotides, and (iii) the methylase has a recognition sequence that includes a GpC dinucleotide;
(e) using terminator-coupled linear amplification to generate extension products from the treated sample, purified DNA, or amplified DNA; and
(f) assaying for the lengths of the extension products of (e) that indicate the methylation status of (i') the one or more control sequence nucleotides and (ii') more than one CpG dinucleotide in the target sequence to thereby determine a number of methylated CpG dinucleotides in the target sequence;
wherein the target sequence is in the sample and wherein (a') methylation at the one or more control sequence nucleotides indicates the presence of the target sequence in the sample before the DNA from the sample is optionally amplified, and the number of methylated CpG dinucleotides indicates the density of DNA methylation in the target sequence, or (b') absence of methylation at the one or more control sequence nucleotides indicates the absence of the target sequence in the sample, purified DNA, or amplified DNA and/or failure of the terminator-coupled linear amplification reaction.

15. The method of claim 14, wherein the methylase preferentially methylates cytosine residues within a recognition sequence that comprises the sequence AGCT, GGCC, GCNGC, or GCGC.

16. A method of evaluating the fraction of polynucleotides comprising a methylated target sequence with an internal control for detecting the presence of the target sequence, the method comprising:
(a) providing a sample that includes DNA, wherein the sample DNA includes a target sequence;
(b) optionally, purifying the DNA to thereby produce purified DNA;
(c) optionally, amplifying the DNA and simultaneously copying the methylation pattern of the DNA to thereby produce amplified DNA;
(d) treating the sample, purified DNA, or amplified DNA with a methylase that preferentially methylates at one or more control sequence nucleotides, wherein (i) the target sequence and the control sequence nucleotide are present in the DNA before the DNA is optionally amplified, (ii) the methylase preferentially methylates cytosines other than cytosines in CpG dinucleotides, and (iii) the methylase has a recognition sequence that includes a GpC dinucleotide;
(e) using terminator-coupled linear amplification to generate extension products that indicate the methylation status of (i') the one or more control sequence nucleotides and (ii') one or more CpG dinucleotides in the target sequence in the treated sample, purified DNA, or amplified DNA;
(f) assaying for the length and amount of each of the extension products of (e) that indicate the methylation status of one or more CpG dinucleotides in the target sequence; and
(g) comparing the amount of each assayed extension product of (f) to a corresponding amount in a standard generated from known amounts of methylated and unmethylated template;
wherein the target sequence is in the sample and wherein (a') methylation at the one or more control sequence nucleotides indicates the presence of the target sequence in the sample before the DNA from the sample is optionally amplified and each corresponding amount in the standard indicates the fraction of polynucleotides in the sample, purified DNA, or amplified DNA that comprises the corresponding methylated CpG dinucleotide in the target sequence, or (b') absence of methylation at the one or more control sequence nucleotides indicates the absence of the target sequence in the sample, purified DNA, or amplified DNA and/or failure of the terminator-coupled linear amplification reaction.

17. The method of claim 16, wherein the methylase preferentially methylates cytosine residues within a recognition sequence that comprises the sequence AGCT, GGCC, GCNGC, or GCGC.

* * * * *

SEQUENCE LISTING

```
<160> NUMBER OF SEQ ID NOS: 15

<210> SEQ ID NO 1
<211> LENGTH: 540
<212> TYPE: DNA
<213> ORGANISM: Homo sapiens
<220> FEATURE:
<221> NAME/KEY: misc_feature
<222> LOCATION: (1)..(540)
<223> OTHER INFORMATION: GPX7 CpG island

<400> SEQUENCE: 1
agaaactgag gtcggagtgg gggcgtgacc aggccagcct aaggccgctg cactaatgag      60
aagctgagct ctcagatttt tgcctccctg tccctgccaa gtcgctgttt cctgggacaa     120
gagggagcct cactgaaacg aactccggtc tcagggggaca gaatcctgaa accctggctc    180
tggggtccgg ggcaggggtg cgctgcctca ggacagacgt tgaaactgag gtccagagcc    240
ggacatccac cgcctgcgga gggaacgaga acgcggcgcg tcctgccttg cgggccgagc    300
ggcgccagag ccgcctcctc ccgccccccg cgctagatcc ccccgccccg tctttgccct    360
cgcgacgccg ccacctccgg aacaagccat ggtggcggcg acggtggcag cggcgtggct    420
gctcctgtgg gctgcggcct gcgcgcagca ggagcaggac ttctacgact tcaaggcggt    480
caacatccgg ggcaaactgg tgtcgctgga gaagtaccgc ggatcggtga gtgcgcgggg    540

<210> SEQ ID NO 2
<211> LENGTH: 420
<212> TYPE: DNA
<213> ORGANISM: Homo sapiens
<220> FEATURE:
<221> NAME/KEY: misc_feature
<222> LOCATION: (1)..(420)
<223> OTHER INFORMATION: GPR147 CpG island

<400> SEQUENCE: 2
accctttccg cgagaagctg accctgcgga aggcgctcgt caccatcgcc gtcatctggg      60
ccctggcgct gctcatcatg tgtccctcgg ccgtcacgct gaccgtcacc cgtgaggagc     120
accacttcat ggtggacgcc cgcaaccgct cctaccgct ctactcctgc tgggaggcct     180
ggcccgagaa gggcatgcgc agggtctaca ccactgtgct cttctcgcac atctacctgg     240
cgccgctggc gctcatcgtg gtcatgtacg cccgcatcgc gcgcaagctc tgccaggccc    300
cgggcccggc ccccgggggc gaggaggctg cggacccgcg agcatcgcgg cgcagagcgc    360
gcgtggtgca catgctggtc atggtggcgc tgttcttcac gctgtcctgg ctgccgctct    420

<210> SEQ ID NO 3
<211> LENGTH: 24
<212> TYPE: DNA
<213> ORGANISM: Artificial
<220> FEATURE:
<223> OTHER INFORMATION: GPX7-NF1 primer
```

```
<400> SEQUENCE: 3
gttgtttttt gggataagag ggag                                              24

<210> SEQ ID NO 4
<211> LENGTH: 26
<212> TYPE: DNA
<213> ORGANISM: Artificial
<220> FEATURE:
<223> OTHER INFORMATION: GPX7-NR1 primer

<400> SEQUENCE: 4
aatcrtaaaa atcctactcc tactac                                            26

<210> SEQ ID NO 5
<211> LENGTH: 24
<212> TYPE: DNA
<213> ORGANISM: Artificial
<220> FEATURE:
<223> OTHER INFORMATION: GPX7-NF2 primer

<400> SEQUENCE: 5
ggatagaatt ttgaaatttt ggtt                                              24

<210> SEQ ID NO 6
<211> LENGTH: 22
<212> TYPE: DNA
<213> ORGANISM: Artificial
<220> FEATURE:
<223> OTHER INFORMATION: GPR147-NF1 primer

<400> SEQUENCE: 6
gagaagttga ttttgyggaa gg                                                22

<210> SEQ ID NO 7
<211> LENGTH: 23
<212> TYPE: DNA
<213> ORGANISM: Artificial
<220> FEATURE:
<223> OTHER INFORMATION: GPR147-NR1 primer

<400> SEQUENCE: 7
ccaccataac caacatatac acc                                               23

<210> SEQ ID NO 8
<211> LENGTH: 24
<212> TYPE: DNA
<213> ORGANISM: Artificial
<220> FEATURE:
<223> OTHER INFORMATION: GPR147-NF2 primer

<400> SEQUENCE: 8
ggttttggyg ttgtttatta tgtg                                              24

<210> SEQ ID NO 9
<211> LENGTH: 450
<212> TYPE: DNA
<213> ORGANISM: Homo sapiens
<220> FEATURE:
<221> NAME/KEY: misc_feature
<222> LOCATION: (1)..(450)
<223> OTHER INFORMATION: GSTP1 CPG island

<400> SEQUENCE: 9
tccctaggcc ccgctgggga cctgggaaag agggaaaggc ttccccggcc agctgcgcgg       60
cgactccggg gactccaggg cgcccctctg cggccgacgc ccggggtgca gcggccgccg      120
```

```
gggctggggc cggcgggagt ccgcgggacc ctccagaaga gcggccggcg ccgtgactca    180
gcactggggc ggagcggggc gggaccaccc ttataaggct cggaggccgc gaggccttcg    240
ctggagtttc gccgccgcag tcttcgccac cagtgagtac gcgcggcccg cgtcccggg     300 gatggggctc agagctccca gcatggggcc aacccgcagc atcaggcccg gctcccggc     360 agggctcctc gcccacctcg agacccggga cgggggccta ggggacccag gacgtcccca    420
gtgccgttag cggctttcag ggggcccgga                                     450
```

```
<210> SEQ ID NO 10
<211> LENGTH: 25
<212> TYPE: DNA
<213> ORGANISM: Artificial
<220> FEATURE:
<223> OTHER INFORMATION: GSTPI_NF1 primer

<400> SEQUENCE: 10
ggatttggga aagagggaaa ggttt                                          25

<210> SEQ ID NO 11
<211> LENGTH: 24
<212> TYPE: DNA
<213> ORGANISM: Artificial
<220> FEATURE:
<223> OTHER INFORMATION: GSTPI_NR1 primer

<400> SEQUENCE: 11
actaaaaact ctaaacccca tccc                                           24

<210> SEQ ID NO 12
<211> LENGTH: 25
<212> TYPE: DNA
<213> ORGANISM: Artificial
<220> FEATURE:
<223> OTHER INFORMATION: GSTPI_BMF1F primer

<400> SEQUENCE: 12
gcgatttcgg ggattttagg gcgtt                                          25

<210> SEQ ID NO 13
<211> LENGTH: 25
<212> TYPE: DNA
<213> ORGANISM: Artificial
<220> FEATURE:
<223> OTHER INFORMATION: GSTPI_BUF1F primer

<400> SEQUENCE: 13
gtgtggtgat tttggggatt ttagg                                          25

<210> SEQ ID NO 14
<211> LENGTH: 43
<212> TYPE: DNA
<213> ORGANISM: Artificial
<220> FEATURE:
<223> OTHER INFORMATION: M13GSTPI_BDF1 primer

<400> SEQUENCE: 14
caggaaacag ctatgacygg ygatttyggg gattttaggg ygt                      43

<210> SEQ ID NO 15
<211> LENGTH: 24
```

```
<212> TYPE: DNA
<213> ORGANISM: Artificial
<220> FEATURE:
<223> OTHER INFORMATION: BDR1b primer

<400> SEQUENCE: 15
actaaaaact ctaaacccca tccc                                              24
```